(12) United States Patent
Bordewick et al.

(10) Patent No.: US 8,074,645 B2
(45) Date of Patent: Dec. 13, 2011

(54) APPARATUS AND METHODS FOR PROVIDING HUMIDITY IN RESPIRATORY THERAPY

(75) Inventors: Steven S. Bordewick, Minneapolis, MN (US); Bruce Bowman, Eden Prairie, MN (US); Holly Larkin, Plymouth, MN (US)

(73) Assignee: Somnetics Global Pte. Ltd., Singapore (SG)

( * ) Notice: Subject to any disclaimer, the term of this patent is extended or adjusted under 35 U.S.C. 154(b) by 1248 days.

(21) Appl. No.: 11/786,391

(22) Filed: Apr. 10, 2007

(65) Prior Publication Data
US 2007/0277825 A1 Dec. 6, 2007

Related U.S. Application Data

(60) Provisional application No. 60/790,671, filed on Apr. 10, 2006.

(51) Int. Cl.
*A61M 11/00* (2006.01)
(52) U.S. Cl. ......... 128/204.15; 128/203.16; 128/204.14; 128/206.21
(58) Field of Classification Search ............. 128/203.12, 128/203.17, 203.27, 204.17, 203.16, 204.15, 128/204.14, 206.21, 204.18, 206.28, 207.12
See application file for complete search history.

(56) References Cited

U.S. PATENT DOCUMENTS

| | | | |
|---|---|---|---|
| 3,721,233 A | 3/1973 | Montgomery et al. | |
| 4,010,748 A * | 3/1977 | Dobritz | 128/203.27 |
| 4,381,267 A | 4/1983 | Jackson | |
| 4,396,015 A * | 8/1983 | Johnson | 128/200.14 |
| 4,644,947 A | 2/1987 | Whitwam et al. | |
| 4,829,998 A * | 5/1989 | Jackson | 128/203.12 |
| 5,054,484 A | 10/1991 | Hebeler, Jr. | |
| 5,349,946 A | 9/1994 | McComb | |
| RE35,339 E | 10/1996 | Rapoport | |
| 5,657,752 A | 8/1997 | Landis et al. | |
| 5,769,071 A | 6/1998 | Turnbull | |
| 5,937,855 A | 8/1999 | Zdrojkowski et al. | |

(Continued)

FOREIGN PATENT DOCUMENTS

BE 439 032 A 8/1940

(Continued)

OTHER PUBLICATIONS

Chinese Office Action dated Apr. 1, 2011 for Chinese Patent Application No. 200780021424.4 (6 pgs).

(Continued)

*Primary Examiner* — Steven Douglas
(74) *Attorney, Agent, or Firm* — Mueting, Raasch & Gebhardt, P.A.

(57) ABSTRACT

The present inventions provide respiratory therapy apparatus that introduce water into the pressurized air delivered to a user during various positive airway pressure therapies and corresponding methods. The respiratory therapy apparatus may be configured to administer one or more positive airway pressure therapies, including: continuous positive airway pressure therapy (CPAP), bi-level positive airway pressure therapy (BPAP), auto positive airway pressure therapy (autoPAP), proportional positive airway pressure therapy (PPAP), and/or other positive airway pressure therapies. The respiratory therapy apparatus may include a user interface that defines an interface passage to communicate pressurized air to the user for inhalation and a humidifier that introduces water into the pressurized air generally at the interface passage. Methods according to the present inventions may include introducing water into the interface passage at one or more humidifier ports disposed about the interface passage.

24 Claims, 9 Drawing Sheets

U.S. PATENT DOCUMENTS

| | | | |
|---|---|---|---|
| 5,954,050 A | 9/1999 | Christopher | |
| 6,095,505 A * | 8/2000 | Miller | 261/130 |
| 6,435,180 B1 | 8/2002 | Hewson et al. | |
| 6,532,960 B1 | 3/2003 | Yurko | |
| 6,634,864 B1 | 10/2003 | Young et al. | |
| 6,644,316 B2 | 11/2003 | Bowman et al. | |
| 6,694,978 B1 | 2/2004 | Bennarsten | |
| 6,766,800 B2 | 7/2004 | Chu et al. | |
| 6,854,465 B2 | 2/2005 | Bordewick et al. | |
| 7,063,086 B2 | 6/2006 | Shahbazpour et al. | |
| 7,066,174 B1 | 6/2006 | Smith et al. | |
| 7,089,941 B2 | 8/2006 | Bordewick et al. | |
| 7,096,864 B1 | 8/2006 | Mayer et al. | |
| 7,156,090 B2 | 1/2007 | Nomori | |
| 7,244,235 B2 | 7/2007 | Bowman et al. | |
| D555,235 S | 11/2007 | Korkowski et al. | |
| 7,487,778 B2 | 2/2009 | Freitag | |
| RE40,806 E * | 6/2009 | Gradon et al. | 128/203.17 |
| 7,588,033 B2 | 9/2009 | Wondka | |
| 7,814,911 B2 | 10/2010 | Bordewick et al. | |
| 2003/0079749 A1 | 5/2003 | Strickland et al. | |
| 2004/0226562 A1 | 11/2004 | Bordewick et al. | |
| 2005/0076906 A1* | 4/2005 | Johnson | 128/204.21 |
| 2006/0037613 A1 | 2/2006 | Kwok et al. | |
| 2006/0081250 A1 | 4/2006 | Bordewick et al. | |
| 2006/0196968 A1 | 9/2006 | Rabin et al. | |
| 2006/0231097 A1 | 10/2006 | Dougherty et al. | |
| 2006/0231102 A1 | 10/2006 | Bordewick et al. | |
| 2007/0277827 A1 | 12/2007 | Bordewick et al. | |
| 2008/0006275 A1 | 1/2008 | Nickelson et al. | |
| 2008/0053451 A1 | 3/2008 | Bordewick et al. | |
| 2008/0099017 A1 | 5/2008 | Bordewick et al. | |
| 2009/0078255 A1 | 3/2009 | Bowman et al. | |
| 2009/0078258 A1 | 3/2009 | Bowman et al. | |
| 2010/0065054 A1 | 3/2010 | Bowman et al. | |

FOREIGN PATENT DOCUMENTS

| | | |
|---|---|---|
| BE | 439 032 | 9/1940 |
| EP | 0 601 708 B1 | 3/2000 |
| EP | 1 655 052 A2 | 5/2006 |
| FR | 2695320 A1 | 3/1994 |
| WO | WO 91/19527 A | 12/1991 |
| WO | WO 99/21602 A1 | 5/1999 |
| WO | WO 02/085417 A | 10/2002 |
| WO | WO 2005/079898 A | 9/2005 |
| WO | WO 2005/079898 A2 | 9/2005 |
| WO | WO 2006/044120 A2 | 4/2006 |
| WO | WO 2007/149446 A2 | 12/2007 |
| WO | WO 2010/096467 A1 | 8/2010 |

OTHER PUBLICATIONS

International Preliminary Report on Patentability for PCT/US2007/008845 (9 pgs).

International Search Report and Written Opinion for PCT/US2007/008845 (12 pgs).

* cited by examiner

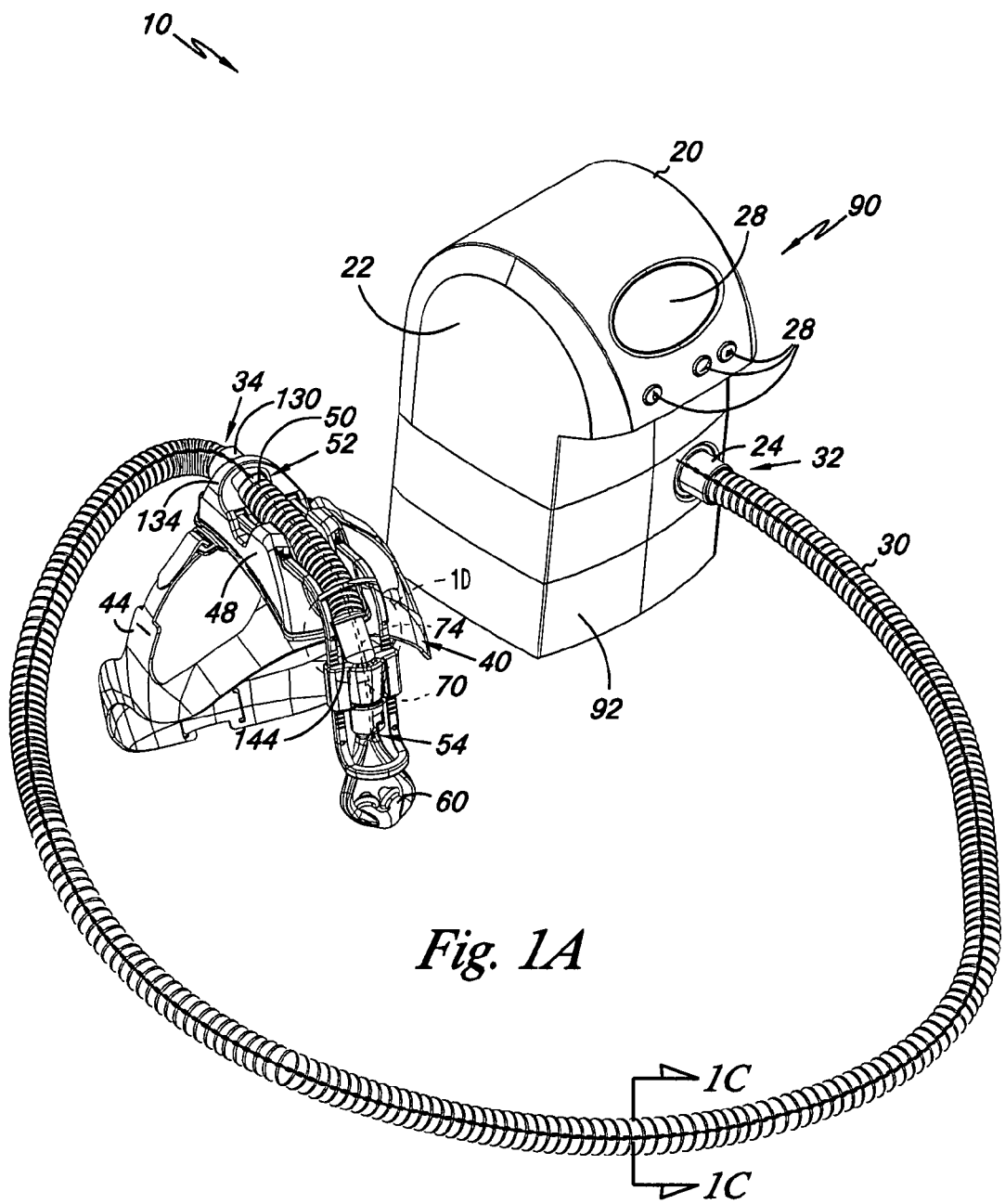
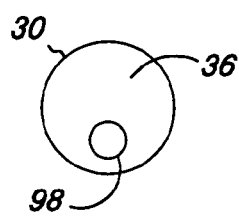
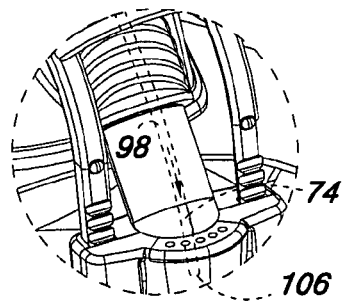
Fig. 1A
Fig. 1C
Fig. 1D

APPARATUS AND METHODS FOR PROVIDING HUMIDITY IN RESPIRATORY THERAPY

CROSS REFERENCE TO RELATED APPLICATIONS

This application claims the benefit under 35 U.S.C. §119 (e) of U.S. Provisional Application Ser. No. 60/790,671, filed on Apr. 10, 2006, the disclosure of which is hereby incorporated by reference in its entirety. A co-pending application filed on Apr. 10, 2007, entitled "APPARATUS AND METHODS FOR ADMINISTRATION OF POSITIVE AIRWAY PRESSURE THERAPIES" by Bordewick et al. is incorporated herein by reference in its entirety.

BACKGROUND OF THE INVENTION

1. Summary of the Invention

The present inventions relate to positive pressurized respiratory therapy and, more particularly, to humidification apparatus and methods for positive pressurize respiratory therapies.

2. Description of the Related Art

Positive airway pressure devices typically deliver pressurized air including air and other breathable gasses to a patient by way of the nose in order to prevent upper airway occlusion during sleep. The pressurized air is typically administered by a mask placed over the user's nose and/or mouth and at a pressure ranging between about 4 cm to 20 cm of water. Positive airway pressure devices have become the devices of choice for the treatment of chronic sleep apnea, chronic pulmonary obstruction and snoring. Many variations of positive airway pressure devices are now commercially available.

A typical positive airway pressure device includes a flow generator, a delivery tube and a mask. In various configurations, the mask may fit over the nose and, sometimes the mouth, may include nasal pieces that fit under the nose, may include nostril inserts into the nares, or some combination thereof. The masks frequently include one or more straps configured to secure the mask to the user.

It may be beneficial to provide water in the pressurized air delivered to the user for therapeutic reasons and also for the comfort of the user. Accordingly, positive airway pressure apparatus may include a humidifier. The humidifier is frequently integrated into the flow generator. Some humidifiers are configured such that the flow generator blows pressurized air over a water reservoir in the flow generator. The pressurized humidified air is then conveyed to the mask through the delivery tube. Typically, the water reservoir must have a large surface area so that a large water reservoir must be provided in the flow generator. In addition, the humidified pressurized air may cool as it passes from the flow generator to the user, which may result in condensation in the delivery tube. Buildup of condensation in the delivery tube may increase flow resistance and may in the extreme occlude delivery of pressurized air.

Therefore, a need exists for a positive airway pressure device that may avoid or reduce condensation of water within the delivery tube.

SUMMARY OF THE INVENTION

Apparatus and methods in accordance with the present inventions may resolve many of the needs and shortcomings discussed above and will provide additional improvements and advantages that may be recognized by those skilled in the art upon review of the present disclosure.

Apparatus in accordance with various aspects of the present inventions may be configured as a respiratory therapy apparatus. The respiratory therapy apparatus may include a flow generator that has an outlet. The flow generator is generally configured to provide pressurized air at the outlet. The respiratory therapy apparatus may further include a user interface. The user interface includes a mask and support bands, and the user interface defines an interface passage. The respiratory therapy apparatus may also include a humidifier configured to introduce water into pressurized air passing through the interface passage.

The present inventions include methods for introducing water into pressurized air provided to a user by a respiratory therapy apparatus. The methods may include providing a humidifier, a flow generator, and a user interface with a mask. The user interface defines an interface passage that may be in fluid communication with the flow generator. The methods may include adapting the humidifier to introduce water into the interface passage.

Other features and advantages of the invention will become apparent from the following detailed description and from the claims.

BRIEF DESCRIPTION OF THE DRAWINGS

FIG. 1A illustrates a perspective view of an exemplary embodiment of a positive airway pressure apparatus in accordance with aspects of the present inventions;

FIG. 1C illustrates a cross-sectional view of portions of an exemplary embodiment of a positive airway pressure apparatus in accordance with aspects of the present inventions;

FIG. 1D illustrates a perspective view of an exemplary embodiment of portions of a user interface in accordance with aspects of the present inventions;

Figure 1B:
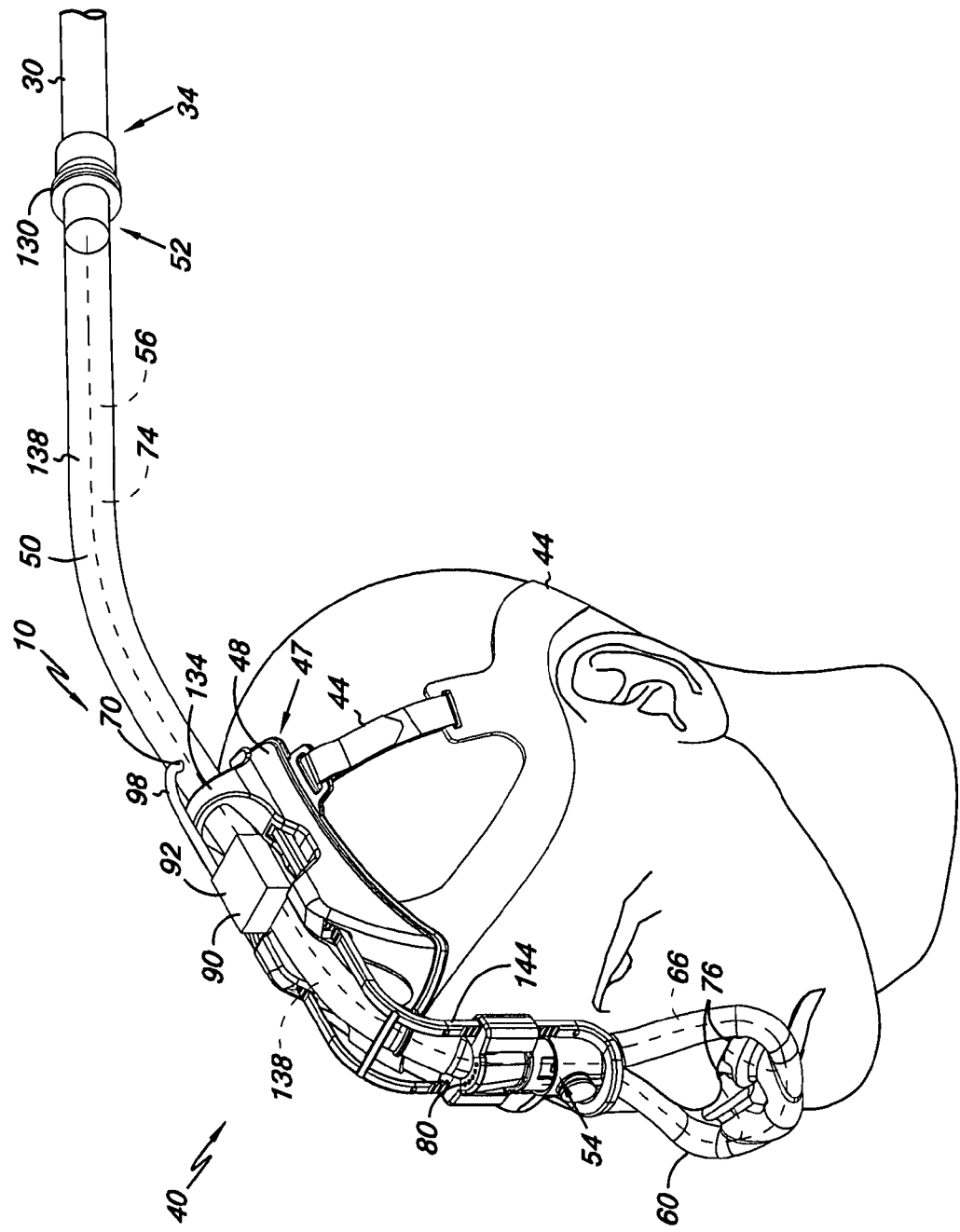
FIG. 1B illustrates a perspective view of an exemplary embodiment of a user interface in accordance with aspects of the present inventions.

All Figures are illustrated for ease of explanation of the basic teachings of the present invention only; the extensions of the Figures with respect to number, position, relationship and dimensions of the parts to form the embodiment will be explained or will be within the skill of the art after the following description has been read and understood. Further, the exact dimensions and dimensional proportions to conform to specific force, weight, strength, flow and similar requirements will likewise be within the skill of the art after the following description has been read and understood.

Where used in various Figures of the drawings, the same numerals designate the same or similar parts. Furthermore, when the terms "top," "bottom," "right," "left," "forward," "rear," "first," "second," "inside," "outside," and similar terms are used, the terms should be understood to reference only the structure shown in the drawings and utilized only to facilitate describing the illustrated embodiments. Similarly, when the terms "proximal," "distal," and similar positional terms are used, the terms should be understood to reference the structures shown in the drawings as they generally correspond with airflow within an apparatus in accordance with the present inventions.

DETAILED DESCRIPTION OF THE INVENTION

The present inventions provide respiratory therapy apparatus 10 and associated methods for treatment of sleep apnea and other respiratory and sleeping disorders. The respiratory therapy apparatus 10 are typically configured to communicate pressurized air to a user lying in bed from a remotely positioned flow generator 20. The respiratory therapy apparatus 10 may include a flow generator 20, a humidifier 90, and a user interface 40. In certain aspects, the respiratory therapy apparatus 10 may also include a delivery tube 30. The flow generator 20 is typically provided as a source of pressurized air. When present, the delivery tube 30 is configured to communicate pressurized air from the flow generator 20 to the user interface 40. The user interface 40 is configured to communicate the pressurized air from the flow generator 20 into the airways of a user. Typically, the user interface 40 is configured to be secured relative to the user's head such that a positive pressure therapy may be administered to a user as the user sleeps. The humidifier 90 is generally configured to humidify the air delivered to the user at the user interface 40. In certain aspects, the humidifier 90 may communicate water into the air at the user interface 40. The humidifier 90 may, in some aspects, be generally disposed about the user interface 40.

The Figures generally illustrate exemplary embodiments of respiratory therapy apparatus 10 in accordance with aspects of the present inventions. The particularly illustrated embodiments of the respiratory therapy apparatus 10 have been chosen for ease of explanation and understanding of various aspects of the present inventions. These illustrated embodiments are not meant to limit the scope of coverage but, instead, to assist in understanding the context of the language used in this specification and in the appended claims. Accordingly, the appended claims may encompass variations of the present inventions that differ from the illustrated embodiments.

Respiratory therapy apparatus 10 in accordance with aspects of the present invention includes a flow generator 20 configured to provide one or more positive airway pressure therapies to a user. The one or more positive airway pressure therapies may include continuous positive airway pressure therapy (CPAP), bilevel positive airway pressure therapy (BPAP), auto positive airway pressure therapy (autoPAP), proportional positive airway pressure therapy (PPAP), and/or other positive airway pressure therapies as will be recognized by those skilled in the art upon review of this disclosure.

The flow generator 20 typically includes a flow generator housing 22 having an outlet 24, with the flow generator 20 adapted to deliver pressurized air to the outlet 24. In order to deliver pressurized air to the outlet 24, the flow generator 20 may include one or more of various motors, fans, pumps, turbines, ducts, inlets, conduits, passages, mufflers, and other components, as will be recognized by those skilled in the art upon review of the present disclosure. A control unit 26 may be included in the respiratory therapy apparatus 10.

The control unit 26 may be adapted to control one or more components of the flow generator 20. The control unit 26 will typically be positioned within or on the flow generator housing 22, but may be otherwise positioned or located, including remotely, as will be recognized by those skilled in the art upon review of the present disclosure. The control unit 26 is operably connected to one or more components of the flow generator 20. The control unit 26 may include one or more circuits and/or may include one or more microprocessors as well as a computer readable memory.

The control unit 26 is typically configured to output one or more control signals to various components of the flow generator 20 and other components of the respiratory therapy apparatus 10. The control unit 26, in some aspects may be adapted to receive one or more signals from one or more components of the respiratory therapy apparatus 10. The control unit 26 may process or otherwise utilize the signals from the components of the respiratory therapy apparatus 10 in formulating the one or more control signals output to various components. The control unit 26 may be particularly adapted to control a humidifier 90, and the control unit 26 may be configured to control the humidifier 90 in response to information entered through the control interface 28. The control unit 26 may be further adapted to control one or more vent valves 84 as well as other components of the respiratory therapy apparatus 10.

In one aspect, the control unit 26 may control the flow generator 20 in response to information including commands from the control interface 28. The control interface 28 may include one or more buttons, switches, touch screens, or other controls for controlling the flow generator 20 and associated components. The control interface 28 may be in communication with the control unit 26 to transfer information to and from the control unit 26. Portions of the control interface 28 may be mounted on the flow generator housing 22 or may be otherwise positioned on components of the apparatus 10 or remotely as will be recognized by those skilled in the art upon review of the present disclosure.

The user interface 40 is generally configured to be secured to a user and to communicate pressurized air into the airway of a user. Typically, the user interface 40 will include at least a mask 60, and one or more support bands 44 to secure the mask 60 to a user. The user interface 40 may define an interface passage 74 that includes at least a chamber of the mask 60 such that pressurized air is communicated through the interface passage 74 for inhalation by the user. The user interface 40 may also include a mount 48 and various other features such as pads that allow the user interface 40 to be affixed to the user and that maintain a proper orientation of the user interface 40 with respect to the user.

The mask 60 may be configured to communicate the pressurized air generated by the flow generator 20 to the user's airways. In various aspects, the mask 60 may be positioned about the user's nose, the user's mouth, or both the user's nose and mouth in order to provide a generally sealed connection to the user for the delivery of pressurized air for inhalation. A pressure greater than atmospheric pressure may be provided within the sealed connection. Accordingly, portions of the mask 60 may be formed of soft silicone rubber or similar material that may provide a seal 76 and that may also be generally comfortable when positioned against the user's skin. In various aspects, the mask 60 may include nasal pieces that fit under the user's nose, nostril inserts into the user's nares, or some combination thereof.

The mask 60 may define an exterior mask surface 62 and an interior mask surface 64. In some aspects, the interior mask surface 64 may define a chamber 66. In other aspects, the interior mask surface 64 may define at least a portion of a chamber 66 when generally sealed about portions of the user's face. The mask 60 typically includes one or more mask inlets 68 through which pressurized air may be communicated into the chamber 66, and one or more seals 76 about which the pressurized air may be generally communicated to the user. In some aspects, pressurized air may be inhaled from the chamber 66 by the user. In some aspects, the pressurized air may pass out of the chamber 66 for inhalation by the user, for example, through one or more apertures 69 surrounded by seals 76.

An interface passage 74 is defined by the user interface 40 such that pressurized air is communicated through the interface passage 74 for inhalation by the user. The interface passage 74 includes the chamber 66 from the mask inlet 68 to the seal 76. The interface passage 74 may further include at least the portions of passageways 138 defined by various tubes, conduits, ducts, channels, and other structures that are included in the user interface 40 so as to be generally secured about the user's head and through which pressurized air may be communicated to the mask inlet 68. In some aspects, the interface passage 74 may extend at least distally from a proximal attachment location 134. The proximal attachment location 134 is the most proximal location at which the passageways 138 defined by various tubes, conduits, channels, and other structures included in the user interface 40 may be secured to the user's head in a generally fixed orientation. In some aspects, support bands 44 may be provided at the proximal attachment location 134. In various other aspects, the proximal attachment location 134 may be at the mount 48, at some support structure 144, that, in turn, is secured to the mount 48 or to support bands 44, combinations thereof, or other securements to the user's head as would be recognized by those skilled in the art upon review of this disclosure. In some aspects, insulation may be provided about the passageways 138 in order to prevent water condensation.

In some aspects, the user interface 40 may include the flow generator 20 such that the flow generator 20 is generally secured about the user's head. The flow generator 20 may communicate with the interface passage 74 to convey pressurized air to the user for inhalation.

In other aspects, the flow generator 20 is separated from the user interface 40. A delivery tube 30 may then be secured to an outlet 24 of the flow generator 20 to convey pressurized air from the flow generator 20 to the user interface 40. In one aspect, the delivery tube 30 may be configured as an elongated flexible tube. The delivery tube 30 may be composed of a lightweight plastic, and often has a ribbed configuration. A delivery tube passage 36 defined by the delivery tube 30 may extend between a proximal end 32 and a distal end 34 of the delivery tube 30. The proximal end 32 of the delivery tube 30 may be adapted to be secured to the flow generator 20 with the delivery tube passage 36 in fluid communication with the outlet 24 of the flow generator 20. The user interface 40 may be secured to the distal end 34 of the delivery tube 30 in fluid communication with the delivery tube passage 36. Accordingly, pressurized air from the flow generator 20 may be conveyed into the delivery tube passage 36 of the delivery tube 30 and delivered to the user interface 40. The distal end 34 of the delivery tube 30 is typically connected to the user interface 40 at a connector 130. In some aspects, the connector 130 may be a rigid structure such as a nipple. In some aspects, the connector 130 may swivel in order to prevent twisting of the delivery tube 30 by the user during sleep.

In certain aspects, the user interface 40 may include a passageway 138 configured as an interface conduit 50. When present, the interface conduit 50 may define an interface conduit proximal end 52, an interface conduit distal end 54, and a lumen 56. The interface conduit 50 may be, for example, a ribbed plastic hose, a plastic or rubber tube, a pipe, or combinations thereof. The user interface 40 is configured such that at least portions of the interface conduit 50 may be generally secured about the user's head. In aspects of the present inventions that include a delivery tube 30, the distal end 34 of the delivery tube 30 may be connected to the interface conduit proximal end 52 so that the delivery tube passage 36 is in fluid communication with the lumen 56, which may allow pressurized air to be delivered from the flow generator 20 to the lumen 56 via the delivery tube passage 36. In aspects of the present inventions wherein the user interface 40 includes the flow generator 20, the interface conduit proximal end 52 may be adapted to the outlet 24 of the flow generator 20 so that pressurized air can be communicated from the flow generator 20 into the lumen 56. The interface conduit distal end 54 may be adapted to the mask 60 so that pressurized air may be delivered from the lumen 56 into the chamber 66 of the mask 60. Accordingly, the interface passage 74 may include at least portions of the lumen 56 of the interface tube as well as the mask inlet 68, and the chamber 66 to the seal 76.

One or more vents 80 including holes, louvers, slots and other openings may be provided to release pressurized air from the interface passage 74 to the ambient atmosphere especially during exhalation by the user to generally purge exhaled air, which may have a high $CO_2$ concentration, from at least portions of the interface passage 74. In various aspects, the one or more vents 80 may be included in the mask 60. In aspects that include the interface conduit 50, the one or more vents 80 may be included in the interface conduit 50, usually generally proximate to the interface conduit distal end 54. The one or more vents 80 may include one or more vent valves 84 positionable between at least a first valve position 86 and a second valve position 88 to control the release of pressurized air through the one or more vents 80. In the first valve position 86, the vent valve 84 may be substantially closed so that air flow through the vent 80 is at a minimum.

Airflow through the vent 80 may be maximal when the vent valve 84 is in the second valve position 88, in which position the vent valve 84 may be substantially open. In certain aspects, the vent valve 84 may be based in MEMS technology. In various aspects, the vent valve 84 may be a butterfly valve, gate, flap, or other as would be recognized by those skilled in the art upon review of this disclosure.

The one or more vent valves 84, in some aspects, may be adapted to alternate between at least the first valve position 86 to retain air and the second valve position 88 to release air including pressurized air and exhaled air in synchronization with the user's breathing cycle. For example, the control unit 26 may be adapted to detect the user's breathing, and to modulate the one or more vent valves 84 in synchronization with the user's breathing cycle between at least the first valve position 86 and the second valve position 88. For example, the one or more vent valves 84 might be positioned in the first valve position 86 during portions of the inhalation portion of the user's breathing cycle and positioned in the second valve position 88 during portions of the exhalation portion of the user's breathing cycle.

In some aspects, the interface conduit 50 may be adapted to maintain a particular orientation with respect to the user such as, for example, being generally offset from the face of the user with the mask 60 apposed to the user only at the nares. Accordingly, the interface conduit 50, in this or other aspects, may include rigid portions having sufficient rigidity to maintain the particular orientation with respect to the user. The rigid portions of the interface conduit 50 may be configured from hard plastics and similar materials or may incorporate various wires and other rigid structural elements or combinations thereof as would be recognized by those skilled in the art upon review of this disclosure. Various support structures 144 may also be secured about the interface conduit 50 in order to maintain the orientation of the interface conduit 50. The support structures 144 may also include various adjustment mechanisms such that the position of the mask 60 may be adjusted with respect to the user's nares, nose, and/or mouth, as would also be recognized by those skilled in the art upon review of this disclosure.

Support bands 44 may be attached to portions of the interface conduit 50, attached to structures that are, in turn, secured to the interface conduit 50, attached to the mask 60, or attached to structures that are, in turn, secured to the mask 60 in order to secure the mask 60 about the user's head. The support bands 44 are typically in the form of elongated members that are configured to exert sufficient tension to retain the interface conduit 50 on the head of the user and, more particularly, to retain the mask 60 generally oriented to deliver pressurized air to the user as the user sleeps. In certain aspects, the support bands 44 are configured as flattened straps to comfortably distribute a force over their surface area. The support bands 44 may be formed from one or more stretchable elastic materials, substantially unstretchable materials, or other materials as will be recognized by those skilled in the art upon review of the present disclosure. The support bands 44 may be integrally formed or interconnected by a variety of mechanical linkages. The support bands 44 may incorporate various buckles, snaps, hook and loop type fasteners, such as that sold under the trade name Velcro®, or other components to link and/or permit relative adjustment of the support bands 44. Various aspects of the support bands 44 may be adjustable by the user to position, inter alia, the interface conduit 50 and mask 60. These aspects may include length, relative positions or other aspects as will be recognized by those skilled in the art upon review of the present disclosure.

In some aspects, the mount 48 provides a generally rigid structure to which portions of the user interface 40 including portions of the interface conduit 50 and one or more of the support bands 44 may be secured to the mount 48. This may secure portions of the interface conduit 50 passing about the mount 48 and extending distally from the mount 48 to the user's head. In some aspects, the flow generator 20 may be at least partly secured to the mount 48 or mounts 48. In some aspects, support structures 144 may be included to secure portions of the interface conduit 50 about the user's head and to maintain an orientation of those portions of the interface conduit 50 with respect to the user's head. The support structures 144 may be secured to the mount 48.

The humidifier 90 is typically configured to introduce water into the pressurized air passing through the interface passage 74 to humidify the pressurized air. Water includes liquid water, water vapor, and combinations of liquid water and water vapor. Water in the form of, for example, water vapor, liquid water droplets, mist, micro-droplets, fog, or various combinations of liquid water and water vapor may be introduced into the pressurized air passing through the interface passage 74 to humidify the pressurized air. The pressurized air may be humidified for therapy, comfort, or other reasons, as will be recognized by those skilled in the art upon review of the present disclosure. In some aspects, the water may include pharmacological and other therapeutic agents so that the humidifier acts as a nebulizer by introducing the pharmacological and other therapeutic agents into the pressurized air passing through the interface passage 74.

The humidifier 90 includes a water source 92 to store water. In some aspects, the water source 92 may be located in the flow generator housing 22. In other aspects, the water source 92 may be separate from the flow generator housing 22, and, for example, may be configured into the user interface 40. The water source 92 is in fluid communication with at least one humidifier port 70 situated to introduce water derived from the water source 92 into the pressurized air within the interface passage 74 at the humidifier port 70. The humidifier port 70 may be anywhere along the interface passage 74 including in the interface conduit 50 or in the mask 60 or combinations thereof. The humidifier port 70 is configured accordingly to allow the introduction of water into the interface passage 74. In some aspects, there may be a plurality of humidifier ports 70 to introduce water at various points along the interface passage 74. The water source 92 may be a reservoir or other source of water. In certain aspects, the water source 92 may be secured to the user interface 40. In some aspects, the water source 92 may include baffles, absorbent materials, or other features to prevent sloshing. The water source 92 may be in fluid communication with the humidifier port 70 by a water tube 98 such that fluid may be conveyed from the water source 92 to the humidifier port 70.

Water flow through various components including the water tube 98 may be gravity driven, at least in part, in some aspects. In various aspects, a pump 96, including a micropump and other devices that transfer energy into a fluid, may be used to convey water from the water source 92 to the humidifier port 70 through the water tube 98 or through other portions of the apparatus 10. Capillary effects may also be used to convey water from the water source 92 through the water tube 98. A pump 96 or series of pumps 96 may also be provided to introduce the water into the pressurized air passing along the interface passage 74 at the humidifier port 70. One or more flow valves 168 may be positioned to regulate the flow of water within the humidifier 90 including the introduction of water into the interface passage 74 at the humidifier port 70. The flow valve 168 may be configured as a needle valve, butterfly valve, globe valve, or other valve. The water may be introduced as, for example, a spray or a vapor, or combinations thereof. Accordingly, various nozzles 106 including sprayers, orifices, jets, vaporizers, and heaters 154, and similar devices and combinations thereof may be provided to introduce the water at the humidifier port 70. In various aspects, the nozzles 106, heaters 154, and similar devices and combinations thereof may be located generally proximate the humidifier port 70. Transducers 158 including ultrasonic, piezo-ceramic, and other transducers may be employed in some aspects, for example, to generate water vapor, micro-droplets, mist, or combinations thereof.

Various aspects may include one or more capillary pumps 94. The one or more capillary pumps 94 may be configured to use heat to convert water generally in the liquid phase to water generally in the vapor phase in some aspects. In various aspects, the capillary pumps 94 may be configured to generate water generally in the form of a mist or in the form of micro-droplets. Heaters 154 may be employed in the humidifier 90 in various ways to facilitate conversion of water generally in the liquid phase to water generally in the vapor phase as would be understood by those skilled in the art upon review of this disclosure. Heaters 154 may be provided at various locations in the humidifier 90. The water generally in the vapor phase may then be introduced into the interface passage 74 at the one or more humidifier ports 70.

In some aspects, an exchange material 110 may be provided in the interface passage 74 at the humidifier port 70. The exchange material 110 may be configured as a mesh, screen, porous material, molecular sieve, or other material that may, for example, attract water by capillary action or may have various surface properties to transport water over the surface. In some aspects, the exchange material 110 may be configured to allow pressurized air to flow through. Water may then be conveyed from the water source 92 through one or more water tubes 98 to the exchange material 110. The exchange material 110 may then collect the water from the one or more water tubes 98, and the water may be introduced into the pressurized air by evaporation as the pressurized air passes about the exchange material 110. In various aspects the exchange material 110 may occupy various portions of the interface passage 74 and the water may be distributed over the exchange material 110 at a plurality of locations. In some aspects, various additives may be included in the water, for example, in order to enhance the capillary action of the exchange material 110 or to enhance evaporation. Heat may be provided to the exchange material 110 and/or to the water in order to enhance evaporation in some aspects.

In some aspects, the humidifier port 70 may be distal of the vent 80, while in other aspects the humidifier port 70 may be proximal of the vent 80. In various aspects, the introduction of water may be periodic. For example, the introduction of water may be synchronized with at least phases of the user's breathing cycle. The phases of the user's breathing cycle may include at least an inhalation phase and an exhalation phase. For example, water may be introduced into the pressurized air at the humidifier port 70 generally during the inhalation phase of the breathing cycle, so that the water is generally delivered to the user. No water is introduced generally during the exhalation portion of the breathing cycle in order to prevent water release through the vents 80 to the ambient atmosphere. Synchronization may provide greater humidification efficiencies by humidification of the inspired air while minimizing wasted humidification of expired air. In various aspects, a measured amount of water may be introduced into the pressurized air at the humidifier port 70 to control the humidity delivered to the user. For example, a measured volume of water could be introduced into the pressurized air at the humidifier port 70 generally during the inhalation phase of the breathing cycle.

In some aspects, the water introduction may be synchronized with the positioning of the vent valves 84 and may also be synchronized with the user's breathing cycle. For example, water may be introduced into the pressurized air at the humidifier port 70 when the one or more vent valves 84 are positioned in the first valve position 86 so that the water is retained for delivery to the user. No water is introduced when the vent valves 84 are positioned in the second valve position 88 because the water might be released through the open vents 80 to the ambient atmosphere. In various aspects, the control unit 26 may be operably connected to the one or more vent valves and may be configured to control the introduction of water into the interface passage 74. The control unit 26 may be configured to detect phases of the user's breathing cycle, to control the introduction of water into the interface passage 74, and to control the position of the vent valves 84 in ways that would be readily recognized by those skilled in the art upon review of this disclosure. In some aspects having a plurality of vent valves 84, the valves may be positioned in harmony, so that, for example, every vent valve 84 is positioned in the first valve position 84. In other aspects having a plurality of vent valves, the valve may be disharmoniously positioned, so that, for example, some of the vent valves 84 may be positioned in the first valve position 84 while other vent valves 84 in the plurality of vent valves 84 may be positioned in the second valve position 86. In various aspects, one or more vent valves may be positionable in positions other than the first valve position 84 and the second valve position 86.

Some aspects of the respiratory therapy apparatus 10 may include a heat and moisture exchanger in addition to the humidifier 90, which may reduce the amount of water that the humidifier 90 introduces in order to meet patient needs. The heat and moisture exchanger typically includes hygroscopically treated material [HME material] to collect heat and water from expired air to warm and humidify the gas subsequently inspired by the user. In some embodiments, the HME material may be positioned distal from the vent 80 to prevent loss of water through the vent 80. For example, the HME material may be placed in a portion of the chamber 66 defined by the mask 60.

In operation, the user interface 40 may be secured to the user's head and the mask 60 positioned with respect to the user's nose and/or mouth. In some aspects, the delivery tube 30 may be secured to the user interface 40 and to the outlet 24 of the flow generator 20. The respiratory therapy apparatus 10 may then be activated. The respiratory therapy apparatus 10 delivers humidified pressurized air to the user in order to provide a respiratory therapy.

FIG. 1A generally illustrates a respiratory therapy apparatus 10 according to the present inventions. As illustrated, the respiratory therapy apparatus 10 includes a flow generator 20, a delivery tube 30, and a user interface 40. The flow generator 20, in this embodiment, has a control interface 28 configured into the flow generator housing 22. Also, in this embodiment, the flow generator 20 includes portions of the humidifier 90.

The proximal end 32 of the delivery tube 30 is attached to the outlet 24 of the flow generator 20, as illustrated in FIG. 1A. In this embodiment, water may be conveyed from the water source 92 in the flow generator 20 and introduced into the pressurized air passing through the interface passage 74 at the humidifier port 70 through a water tube 98, which may be located within the delivery tube 30. A cross-section of the delivery tube 30 is illustrated in FIG. 1C, which shows the water tube 98 within the delivery tube passage 36. The water tube 98, in this embodiment, is adapted to convey water from the water source 92 to a humidifier port 70 in the interface passage 74 at the user interface 40. The water is then introduced into the interface passage 74 through a nozzle 106, as shown in FIG. 1D. In other embodiments, the water tube 98 may be external to the delivery tube 30, and may be secured to the delivery tube 30 by, for example, various snaps, clips, and pre-molded hooks or clips.

A passageway 138 within the user interface 40 is defined by an interface conduit 50, in this embodiment. The distal end 34 of the delivery tube 30 is attached to the interface conduit proximal end 52 in the illustration at a connector 130. The interface conduit 50 is secured to support structures 144 which are, in turn, secured to the mount 48 to form a portion of the user interface 40. The portion of the interface conduit 50 distal of the proximal attachment location 134 is generally secured to the head of the user and may be generally secured in a particular orientation with respect to the head of the user. As illustrated, the interface conduit 50 is cantilevered from the mount 48 and angled so that the mask 60 may be sealed about the user's nares without the interface conduit 50 touching the user's face. The user interface 40 includes support bands 44 that may be used to secure the user interface 40 about the user's head. In FIG. 1A, the interface conduit distal end 54 is illustrated as attached to the mask 60. The mask 60 is configured to be sealed about the user's nares and to generally touch the user's face generally proximate the nares.

FIG. 1B illustrates a perspective view of portions of the respiratory therapy apparatus 10 including the user interface 40 secured about the user's head. Aspects of the humidifier 90 including the water source 92 are also illustrated in FIG. 1B. A passageway 138 within the user interface 40 is defined by an interface conduit 50, in this embodiment. In this Figure, the interface conduit 50 extends proximal to the user, and the interface conduit proximal end 52 is attached to the distal end 34 of the delivery tube 30 by a connector 130. The interface conduit distal end 54 is joined to the mask 60. The mask 60 is configured to seal about the user's nares at the seals 76, as illustrated. The interface conduit 50 is generally held in a specific orientation by the support structure 144 distal of the proximal attachment location 134. The proximal attachment location 134, as illustrated, is near the mount proximal end 47 where the interface conduit 50 is secured to the mount 48. The interface conduit 50 is cantilevered from the mount 48 in such a way that the interface conduit 50 is securely held generally away from the user's face. Only portions of the mask 60 contact the user's face generally about the nares in this embodiment. Accordingly, at least portions of the interface conduit 50 extending distal of the proximal attachment location 134 are integral with the user interface 40 and define a portion of the interface passage 74. Vents 80 are also provided in the interface conduit 50 generally toward the interface conduit distal end 54 that may generally purge exhaled air. Support bands 44 are attached to the mount 48 to secure the user interface 40 about the user's head. In this embodiment, the water source 92 is attached to the mount 48 to provide a source of water for the humidifier 90. The interface passage 74, as delineated in this Figure, may start at the interface conduit proximal end 52 to include the lumen 56 of the interface conduit 50 and the chamber 66 of the mask 60, and terminating at the intersection of the mask 60 with the user's nares.

Portions of the humidifier 90 including the water source 92 are secured to the mount 48 in the embodiment of FIG. 1B. In this embodiment, water may then be conveyed from the water source 92 through the water tube 98 to the humidifier port 70. In this particular embodiment, the humidifier port 70 is proximal to the proximal attachment location 134 and the humidifier port 70 is proximal to the vents 80. Water may be introduced into pressurized air passing along the interface passage 74 at the humidifier port 70. In other embodiments, the humidifier port may be distal to the proximal attachment location 134, within the mask 60, or anywhere along the interface conduit 50.

Figure 2:
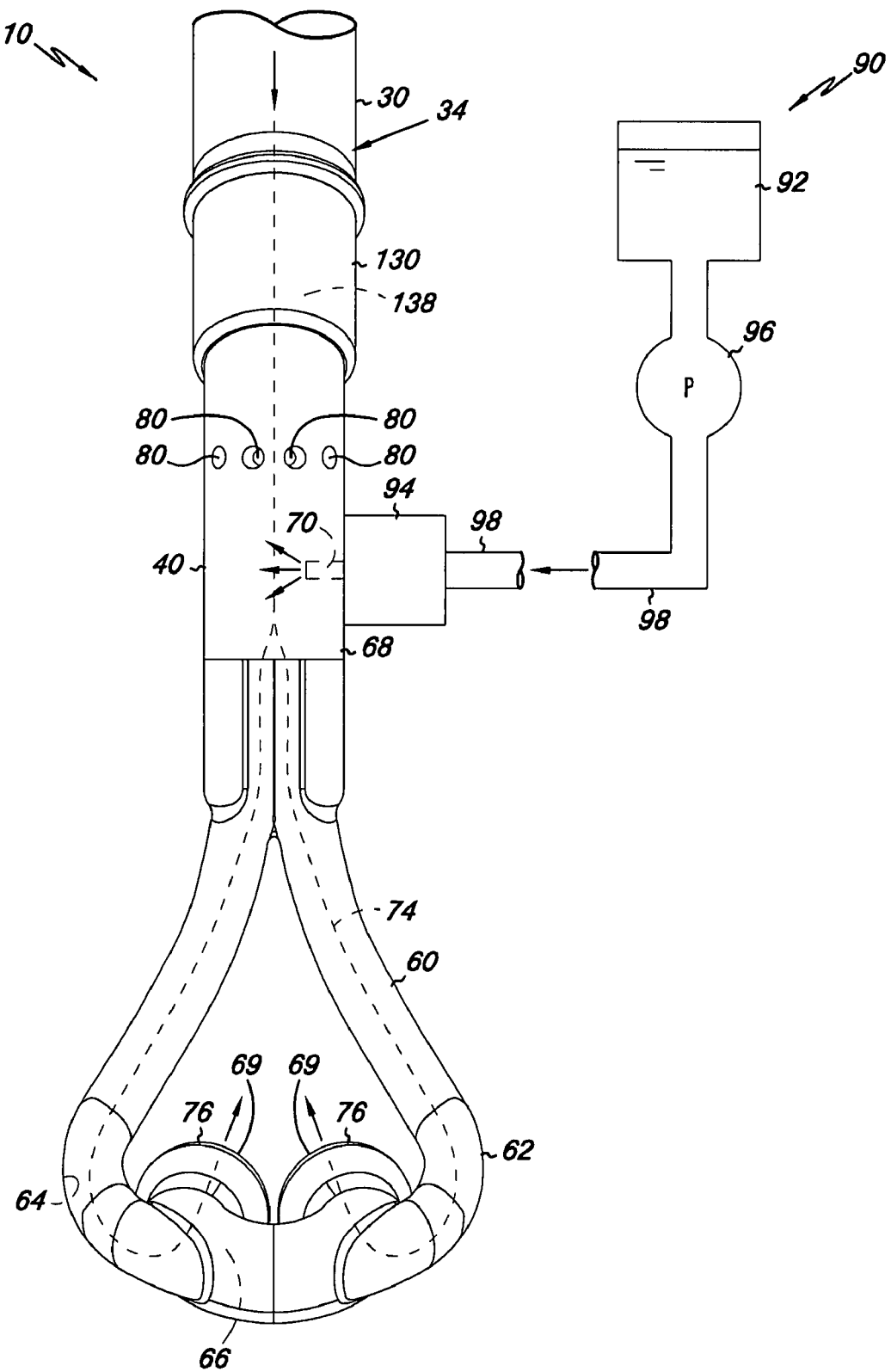
FIG. 2 illustrates a schematic of an exemplary embodiment of a positive airway pressure apparatus in accordance with aspects of the present inventions.

FIG. 2 illustrates an embodiment of portions of the respiratory therapy apparatus 10 including the humidifier 90. In this embodiment, the passageway 138 is defined by a portion of the user interface 40 secured to the mask 60. The portion of the user interface 40 that defines the passageway 138 in this embodiment may be generally configured to be secured to the user's head, so that the passageway 138 is generally in a fixed orientation with respect to the user's head. The mask 60, as illustrated, is configured to seal about the user's nares in order to deliver pressurized air to the user for inhalation. Pressurized air passes along the interface passage 74 including the passageway 138 defined by the portion of the user interface 40, through the mask inlet 68, into the chamber 66, and exits through apertures 69 surrounded by seals 76 into the user's nares. The arrows in this and subsequent figures may be generally indicative of the flow of pressurized air or the flow of water. Vents 80 for the release of excess pressurized air are located in the passageway 138 generally near the mask 60 in this embodiment. The vents 80, in this embodiment, are configured as a series of holes about the circumference of the interface conduit 50. A portion of the interface passage 74 generally near the interface conduit distal end 54 and the chamber 66 is also illustrated.

As illustrated in FIG. 2, water may be delivered from the water source 92 to a capillary pump 94 by a water tube 98. The water source 92 may be positioned at any convenient location about the respiratory therapy apparatus 10. In this illustrated embodiment, one or more pumps 96 are provided to pump the water in liquid phase from the water source 92 through the water tube 98 to the capillary pump 94. The capillary pump 94, as illustrated, introduces the water into pressurized air passing through the lumen 56 of the interface conduit 50 at the introduction point generally as a vapor with the introduction point configured accordingly. The water may then be conveyed along the interface passage 74 through the remainder of the interface conduit 50, through the mask 60, and into the user's nares at the points of inhalation along with pressurized air conveyed from the flow generator 20. In this embodiment, the introduction point is distal of the vents 80 so that water introduced at the introduction point may be more likely to pass into the user's nares and less likely to escape through the vents 80.

Figure 3:
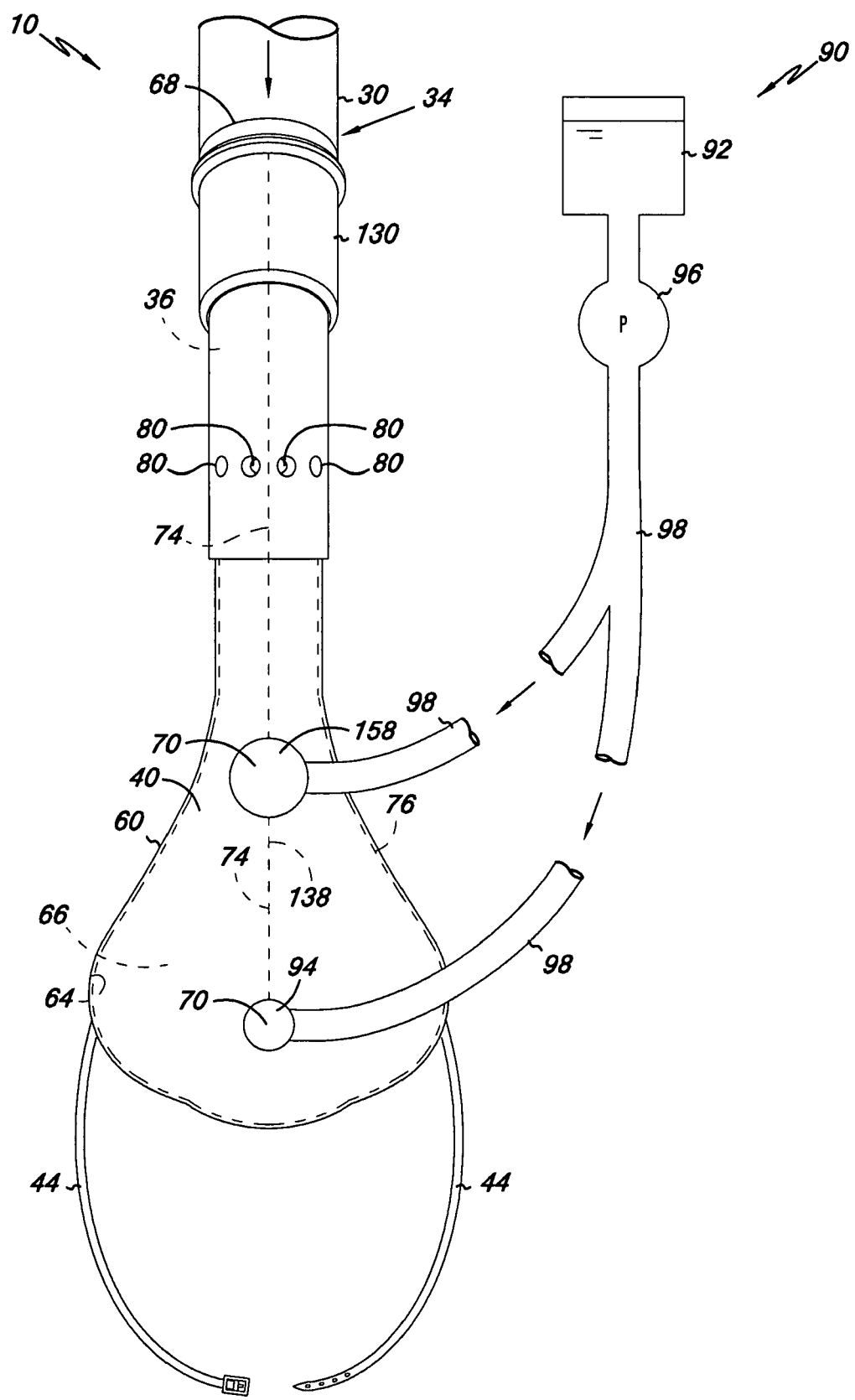
FIG. 3 illustrates another schematic of an exemplary embodiment of a positive airway pressure apparatus in accordance with aspects of the present inventions.

FIG. 3 illustrates another embodiment of portions of the respiratory therapy apparatus 10 including the humidifier 90. In this embodiment, the distal end 34 of the delivery tube 30 is secured to the mask 60 at a connector 130 that generally forms the mask inlet 68. The connector, in this embodiment, may allow the delivery tube to swivel in order to avoid kinks and twists in the delivery tube while allowing the user interface 40 including the mask 60 to maintain a generally fixed orientation with respect to the user. The mask 60, as illustrated, is configured to be secured about the user's nose and mouth so that the user may breathe pressurized air either through the nose or through the mouth. The mask 60 includes the seal 76 around the periphery of the mask 60 to contact the user's face. Support bands 44 are attached to the mask 60 in this embodiment to generally sealably secure the mask 60 to the user's face. In this embodiment, the mask 60 includes vents 80 configured as a series of holes, which are disposed about the mask 60 for the release of pressurized air during exhalation by the user. Pressurized air passes along delivery tube passage 36 and into the user interface 40 at the proximal end of the connector 130, through the mask inlet 68, and into the chamber 66 where the pressurized air may be breathed by the user. The chamber 66, in this embodiment, is defined in part by the interior surface of the mask 60 and, in part, by the user's face when the mask 60 is sealably secured to the user's face. The interface passage 74 may extend from the mask inlet 68 through the chamber 66 in this embodiment.

As illustrated in FIG. 3, water may be conveyed from the water source 92 through water tubes 98 to capillary pump 94 by pump 96. The capillary pump 94 in this embodiment is positioned proximate the humidifier port 70 on the mask 60. The capillary pump 94 introduces water into the interface passage 74 where the water may mix with the pressurized air and be inhaled by the user. The second humidifier port 70, in this embodiment, includes the transducer 158 that may convert liquid water into microdroplets and/or water vapor, which may then be introduced into the interface passage 74.

Figure 4A:
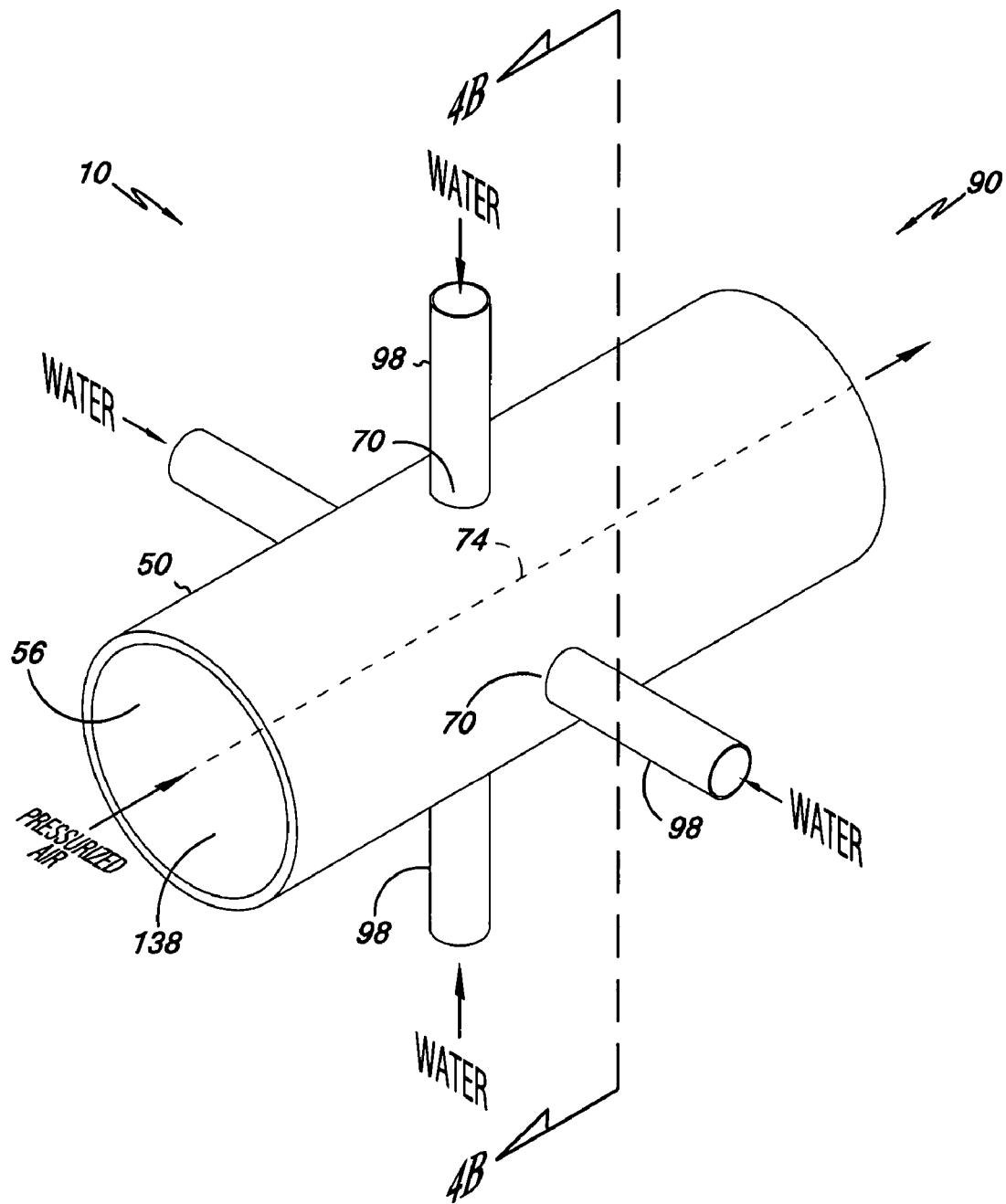
FIG. 4A illustrates a side view of an exemplary embodiment of a portion of a user interface in accordance with aspects of the present inventions.
Figure 4B:
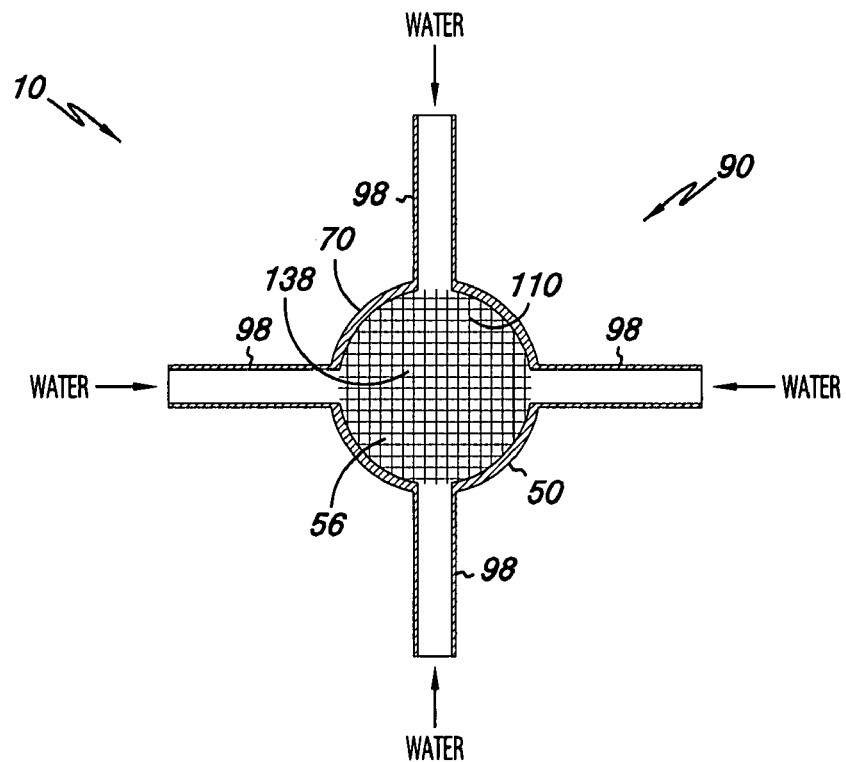
FIG. 4B illustrates an end view of an exemplary embodiment of a portion of a user interface in accordance with aspects of the present inventions.
Figure 4C:
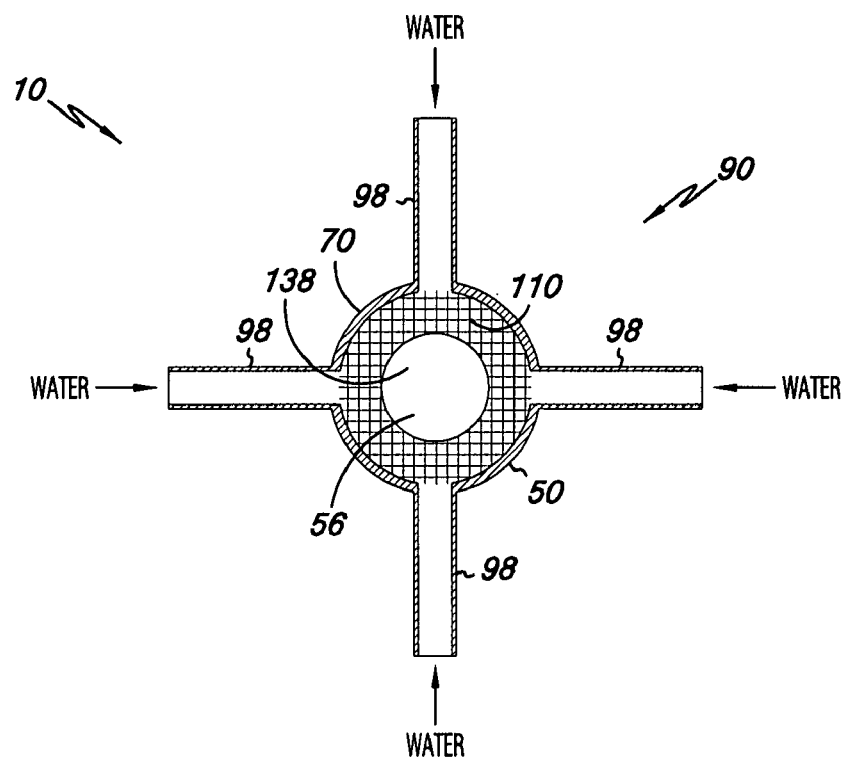
FIG. 4C illustrates an end view of another exemplary embodiment of a portion of a user interface in accordance with aspects of the present inventions.

FIGS. 4A, 4B, and 4C illustrate a portion of the passageway 138 defined by an interface conduit incorporated into the user interface. The illustrated portion of the interface conduit 50 includes an exchange material 110 generally disposed about the humidifier port 70. In this embodiment, the humidifier 90 introduces water from the water source 92 onto the exchange material 110. The exchange material 110 is positioned in the lumen 56 of the interface conduit 50 and configured such that pressurized air may pass through the exchange material 110 along the interface passage 74 to evaporate the water from the exchange material 110 as illustrated in the cross-section of FIG. 4B. In an alternative embodiment, the exchange material 110 may be placed circumferentially about the lumen 56, as illustrated in FIG. 4C. Water may be introduced from the exchange material 110 into the pressurized air generally by evaporation, as illustrated. In these embodiments, several water tubes 98 are disposed generally about the circumference of the interface conduit 50 at the humidifier port 70 to introduce water onto the exchange material 110. The exchange material 110 may collect the water by capillary action. In various embodiments, water tubes 98 may be distributed generally longitudinally along the interface conduit 50 as well as circumferentially.

Figure 5A:
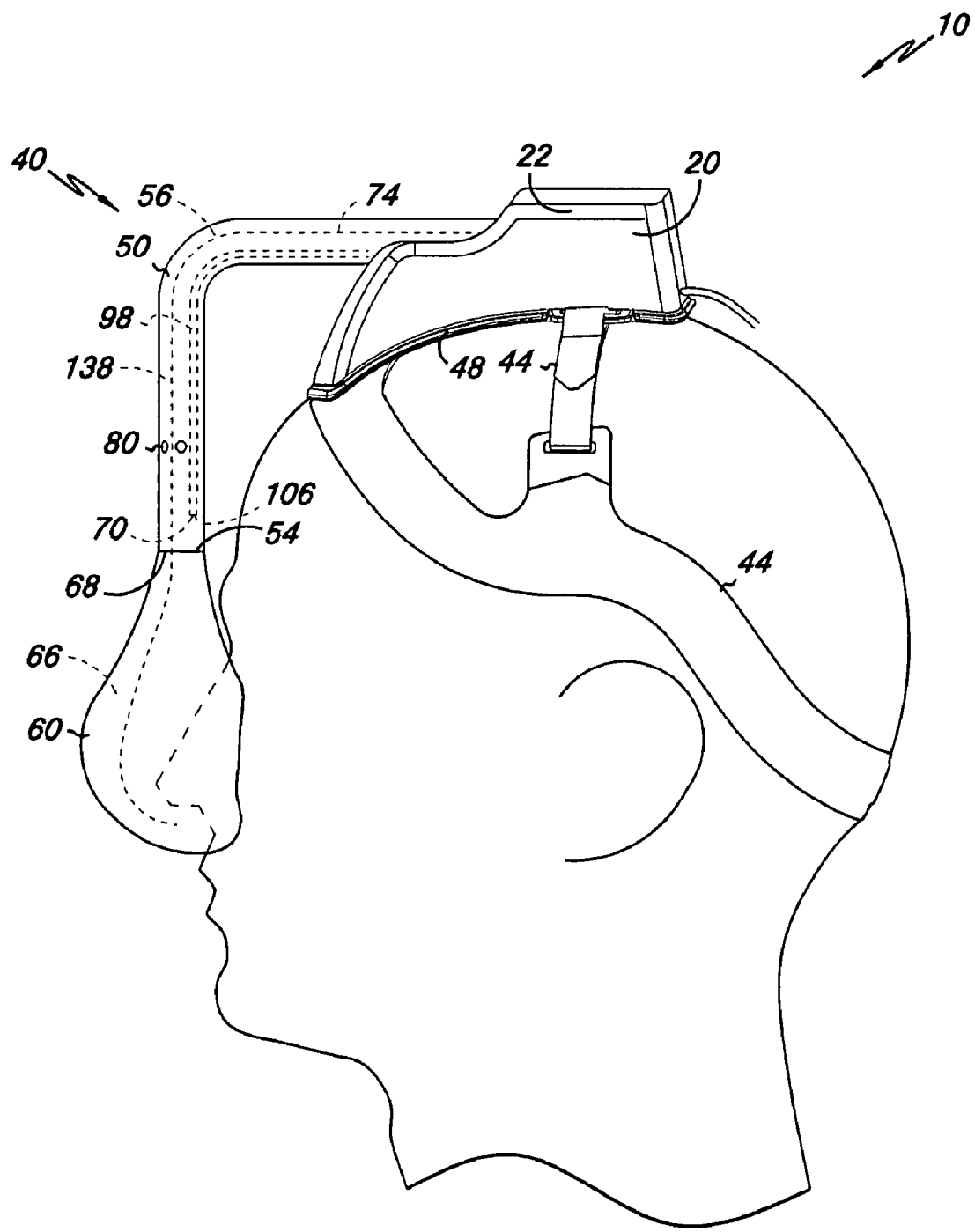
FIG. 5A illustrates a side view of an exemplary embodiment of a positive airway pressure apparatus in accordance with aspects of the present inventions.
Figure 5B:
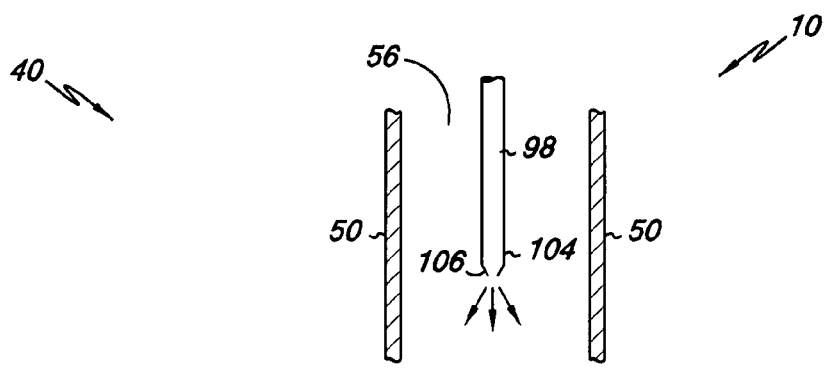
FIG. 5B illustrates a cross sectional side view of another exemplary embodiment of a portion of a user interface in accordance with aspects of the present inventions.

The embodiment illustrated in FIGS. 5A and 5B includes a flow generator 20 that is attached to the user interface 40 generally about the mount 48. A plurality of support bands 44 are provided to secure the user interface 40 including the flow generator 20 about the user's head. A passageway 138 extending from the flow generator housing 22 to the mask 60 is defined by the interface conduit 50 and is maintained in a generally fixed orientation with respect to the user's head in this illustrated embodiment. The interface conduit 50 is shown as extending from the flow generator housing 22 and bending to pass over the user's face without touching the user's face and is generally in a fixed orientation with respect to the user's head including the face. The interface conduit distal end 54 is secured to the mask 60, as illustrated. The interface passage, in this embodiment, includes the passageway 138, the mask inlet 68, and the chamber 66 of the mask 60. Vents 80 are included along the interface passage 74 in the interface conduit 50, as illustrated. The mask 60, in this embodiment, may be sealed about the user's nares to deliver pressurized air for breathing by the user.

In the embodiment illustrated in FIGS. 5A and 5B, portions of the humidifier 90 are located within the flow generator housing 22. These portions of the humidifier 90 may include the water source 92 and one or more pumps 96 to convey water. The passageway 138 is configured as an interface conduit 50 in this embodiment. The water tube 98 extends distally from the flow generator 20 within the lumen 56 defined by the interface conduit 50 to introduce the water into the interface passage 74. The water tube distal end 104, as illustrated, is located distal of the vents 80 within the lumen 56. In this embodiment, water may be introduced into the water tube 98 within the flow generator housing 22, conveyed by the water tube 98 through portions of the lumen 56, and introduced out of the water tube distal end 104 into pressurized air passing though the lumen 56 to humidify the pressurized air. The water tube distal end 104 defines the humidifier port 70 and may be configured as a nozzle 106 to introduce the water by spraying, as illustrated, or in various other ways as would be understood by those skilled in the art upon review of this disclosure. The humidified pressurized air may then pass through the mask 60 and into the user's airways. In various embodiments, the water tube 98 may be configured to introduce water into the interface passage 74 at any location along the interface passage 74.

Figure 6A:
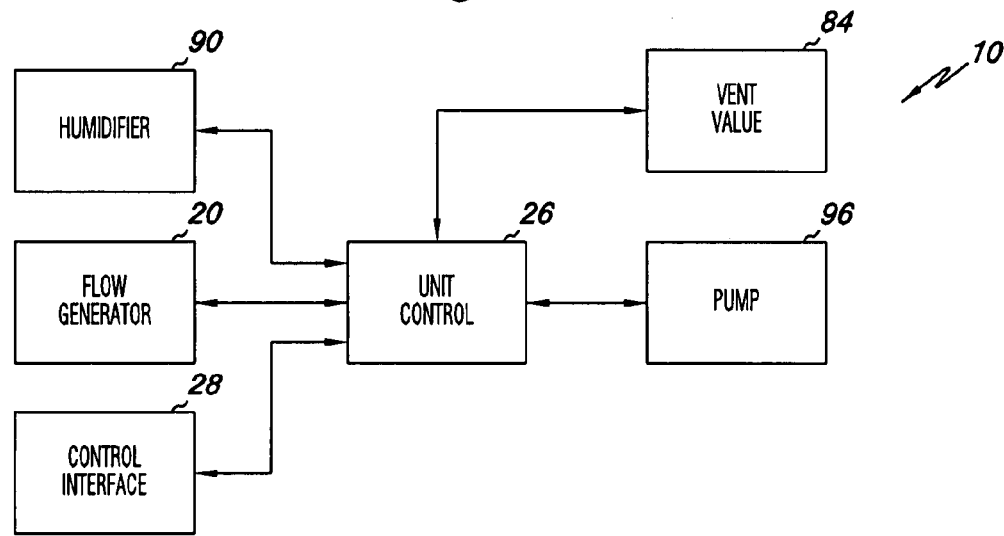
FIG. 6A is a schematic diagram of an exemplary embodiment of a control configuration in accordance with aspects of the present inventions.
Figures 6B, 6C:
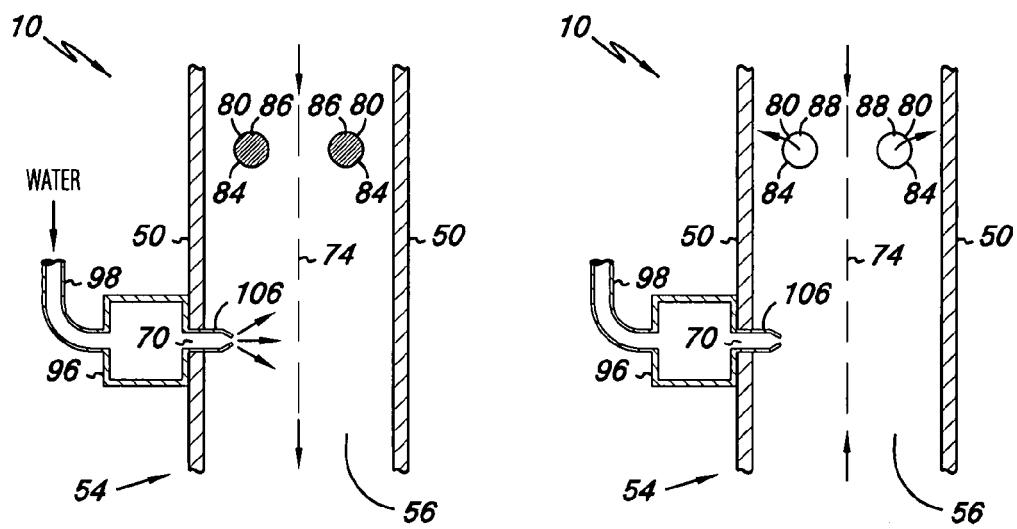
FIG. 6B illustrates a side view of another exemplary embodiment of a portion of a user interface in accordance with aspects of the present inventions.
FIG. 6C illustrates a side view of another exemplary embodiment of a portion of a user interface in accordance with aspects of the present inventions.

FIGS. 6A, 6B, and 6C illustrate the control unit 26 in communication with vent valves 84 positioned at vents 80, with the pump 96 proximate the humidifier port 70, with the humidifier 90 generally, with the flow generator 20, and with the control interface 28. Communication may be by wire, may be wireless such as by Bluetooth® or other wireless protocols, or combinations thereof. In this embodiment, the humidifier port 70 is in the interface conduit 50 distal of the vents 80. As illustrated, the control unit 26 detects at least inhalation and exhalation in order to synchronize valve closures and the introduction of water pulses by the pump 96 with inhalations and valve opening with exhalations. In other embodiments, the control unit 26 may detect other features of the breathing cycle and synchronize the valves 84 to various portions of the breathing cycle. The control unit 26 may accept inputs from the user interface 28 and may also control the flow generator 20 and control the humidifier 90 generally in various ways that would be recognized by those of skill in the art upon review of this disclosure.

During inhalation, the pressurized air passes generally in the direction of the interface conduit distal end 54, as illustrated in FIG. 6B. The vent valves 84, as illustrated, are placed in the first valve position 86 during inhalation and a pulse of water in the form of a jet from the nozzle 106 is introduced into the pressurized air passing along the interface passage 74 by the pump 96 as directed by the control unit 26. The pulse of water humidifies the pressurized air. The humidified pressurized air may then pass along the interface passage 74 for inhalation by the user.

During exhalation, as illustrated in FIG. 6C, at least a portion of the air exhaled by the user may pass into the lumen 56 of the interface conduit 50. The control unit 26 positions the vent valves 84 in the second valve position 88 during exhalation so that the exhaled air along with pressurized air may then exit through the vents 80. No water is introduced during exhalation, as such water may be conveyed out the vents 80 into the ambient atmosphere.

Figure 7A:
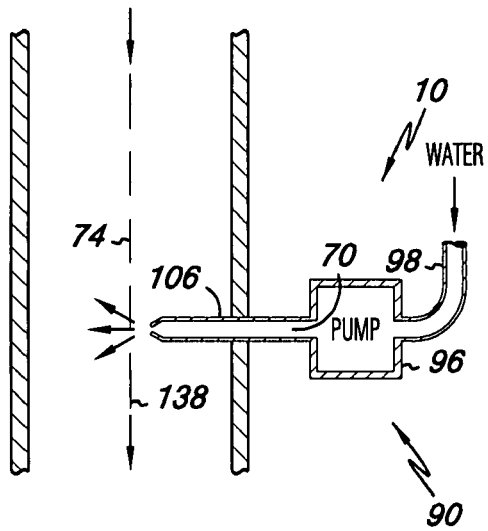
FIG. 7A illustrates a cut-away view of an exemplary embodiment of a portion of a humidifier in accordance with aspects of the present invention.
Figure 7B:
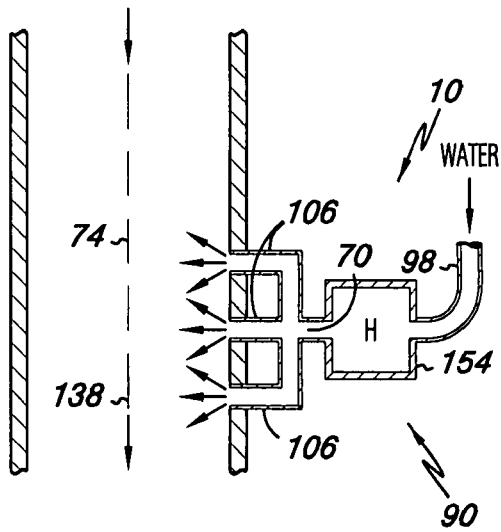
FIG. 7B illustrates a cut-away view of a second exemplary embodiment of a portion of a humidifier in accordance with aspects of the present invention; and, FIG. 7C illustrates a cut-away view of a third exemplary embodiment of a portion of a humidifier in accordance with aspects of the present invention; and, FIG. 7D illustrates a cut-away view of a fourth exemplary embodiment of a portion of a humidifier in accordance with aspects of the present invention.
Figure 7C:
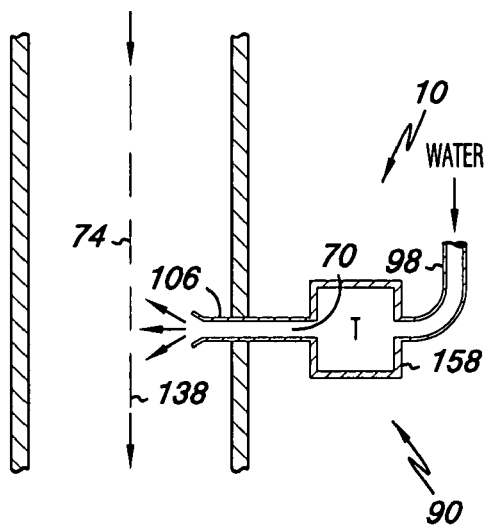
Figure 7D:
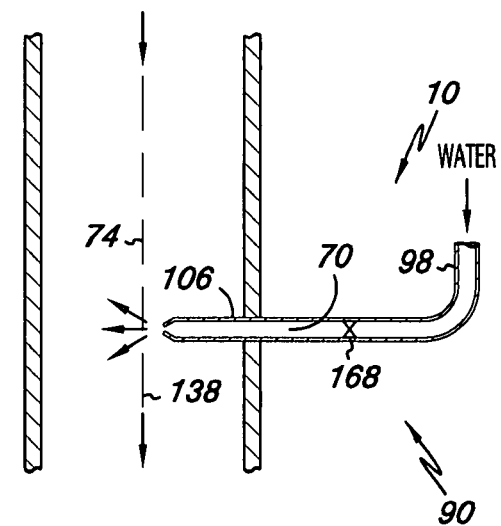

FIGS. 7A, 7B, 7C, and 7D illustrate embodiments of portions of the humidifier 90. The embodiment illustrated in FIG. 7A illustrates the pump 96 configured to introduce water into the interface passage 74 through humidifier port 70 that includes the nozzle 106. In the embodiment illustrated in FIG. 7B, the water may be heated by the heater 154 prior to introduction into the interface passage 74. The humidifier port 70 includes a plurality of nozzles 106 configured as orifices in this embodiment. The embodiment illustrated in FIG. 7C includes the transducer 158. Water passes through the transducer 158 and is introduced through the humidifier port 70. Water flow through the water tube 98 may be gravity driven in the embodiment illustrated in FIG. 7D. In this embodiment, the introduction of water into the interface passage through nozzle 106 may be regulated by flow valve 168.

The present inventions also provide methods for introducing water into the pressurized air provided by the respiratory therapy apparatus 10. The methods include providing a respiratory therapy apparatus 10 including a flow generator 20 for generating pressurized air and a user interface 40 including a mask 60 for delivering the pressurized air to the user for inhalation. The mask 60 defines at least a portion of a chamber 66. The mask 60 includes a mask inlet 68 and a seal 76. The methods may include communicating pressurized air through the interface passage 74 defined by the user interface 40 for inhalation by the user. The interface passage 74 includes the chamber 66. The interface passage 74 may further include at least the portions of passageways 138 defined by various tubes, conduits, ducts, channels, and other structures that are included in the user interface 40 so as to be generally secured about the user's head and through which pressurized air may be communicated to the mask inlet 68. The methods may include providing a humidifier 90, and configuring the humidifier 90 to introduce water into pressurized air passing along the interface passage 74. The methods may further include introducing water into the interface passage 74.

Some methods may also include providing a delivery tube 30 for conveying pressurized air from the flow generator 20 to the interface passage 74 defined by the user interface 40. In some aspects, water may be introduced at multiple humidifier ports 70 along the interface passage 74. In some aspects, the methods may include providing a water source 92. In certain aspects, the methods may include providing one or more pumps 96 to deliver the water from the water source 92 to the humidifier port 70. In certain aspects, the methods may include providing one or more capillary pumps 94. Various aspects may include providing one or more pumps 96 to introduce water into the interface passage 74. Various aspects may include providing one or more transducers 158 to introduce water into the interface passage 74. Various aspects may include providing one or more heaters 154 for use in the introduction of water into the interface passage 74. Various aspects may include providing one or more flow valves 168 for regulating the introduction of water into the interface passage 74. Various aspects may include providing one or more capillary pumps 94 for introducing water into the interface passage 74. In some aspects, the methods may include providing an exchange material 110, the exchange material 110 generally disposed in the interface passage 74, applying the water to the exchange material 110, and evaporating and/or otherwise introducing the water from the exchange material 110 into the pressurized air passing through the interface passage 74. In some aspects, the methods may include providing a nozzle 106 and introducing the water into the pressurized air passing through the interface passage 74 through the nozzle 106. In various aspects, the methods may include introducing the water into the pressurized air passing through the interface passage 74 generally in vapor phase, generally in liquid phase, or generally in combinations of liquid and vapor phases.

Certain aspects may involve providing one or more vents in the interface passage 74 and introducing the water distal of the one or more vents 80, proximal of the one or more vents 80, or both distal and proximal of the one or more vents 80. Some aspects may further include providing one or more vent valves 84 and may also include controlling the one or more vent valves 84 by the control unit 26 to alter the one or more vent valves 84 between a first valve position 86 and a second valve position 88. The control unit 26 may be configured to detect user inhalation and user exhalation and to alter the one or more vent valves 84 between the first valve position 86 and the second valve position 88 generally in synchronization with user inhalation and user exhalation. The control unit 26 may be configured to introduce water into the interface passage 74 during user inhalation.

The foregoing discussion discloses and describes merely exemplary embodiments of the present inventions. Upon review of the specification, one skilled in the art will readily recognize from such discussion, and from the accompanying figures and claims, that various changes, modifications and variations can be made therein without departing from the spirit and scope of the invention as defined in the following claims.

We claim:

1. Apparatus for providing positive airway pressure for the treatment of sleep apnea, chronic pulmonary obstruction and snoring, the apparatus comprising:
    a flow generator configured to provide air at a pressure of 4-20 cm of water at an outlet;
    a user interface comprising support bands configured to retain the user interface on the head of a user, an interface passage in fluid communication with the flow generator outlet and having a lumen, and a mask having a chamber and connected to the interface passage so that pressurized air may be delivered from the lumen into the chamber of the mask, the mask being configured to be positioned in communication with an airway of the user to provide a generally sealed connection to the user for the delivery of the pressurized air for inhalation, the interface passage having at least one vent therein; and
    a humidifier configured to introduce water into the interface passage at a position distal to the flow generator, and distal the at least one vent.

2. The apparatus of claim 1, further comprising the humidifier configured to introduce water vapor into the pressurized air passing through the interface passage.

3. The apparatus of claim 1, further comprising the humidifier configured to introduce at least one of liquid water droplets, mist, micro-droplets, fog, and a combination of liquid water and water vapor into the pressurized air passing through the interface passage.

4. The apparatus of claim 1, further comprising the humidifier configured to introduce water through at least one humidifier port into an interface conduit defining a proximal portion of the interface passage.

5. The apparatus of claim 1, further comprising the humidifier configured to introduce water through a humidifier port into the chamber of the mask defining a distal portion of the interface passage.

6. The apparatus of claim 1, further comprising the humidifier configured to introduce water via a plurality of humidifier ports at points along the interface passage.

7. The apparatus of claim 5, wherein the humidifier comprises a water source in fluid communication with the humidifier port by a water tube such that water may be conveyed from the water source to the humidifier port.

8. The apparatus of claim 7, further comprising a pump connected to the water tube to convey water from the water source to the humidifier port through the water tube.

9. The apparatus of claim 7, further comprising a series of pumps connected to the water tube to convey water from the water source to the humidifier port through the water tube.

10. The apparatus of claim 8, further comprising one or more capillary pumps configured to heat water to convert at least some of the water from the liquid phase into the vapor phase.

11. The apparatus of claim 4, wherein the humidifier port comprises a nozzle.

12. The apparatus of claim 1, wherein the humidifier is configured to introduce the water from a water source into the interface passage at a humidifier port, and wherein the apparatus further comprises an exchange material positioned in the interface passage at the humidifier port.

13. The apparatus of claim 12, wherein at least some of the exchange material is positioned in the interface passage so that the pressurized air flows at least one of through and about the exchange material, the water being directed from the water source through one or more water tubes to the exchange material, the exchange material collecting the water from the one or more water tubes, and wherein the water is introduced into the pressurized air by evaporation as the pressurized air passes at least one of through and about the exchange material.

14. The apparatus of claim 4, wherein the at least one vent is provided in the interface conduit generally proximate a distal end of the interface conduit, and wherein the humidifier port is distal of the vent.

15. The apparatus of claim 1, wherein the at least one vent includes one or more vent valves having a first valve position and a second valve position to control the release of the pressurized air through the at least one vent, in the first valve position the vent valve being substantially closed so that air flow through the vent is at a minimum, and in the second valve position the vent valve being substantially open so that air flow through the vent is at a maximum.

16. The apparatus of claim 1, further comprising the humidifier configured so that introduction of water is periodic.

17. The apparatus of claim 16, further comprising the humidifier configured so that water is introduced into the interface passage during the inhalation phase of the breathing cycle and not during at least a portion of the exhalation portion of the breathing cycle.

18. The apparatus of claim 1, further comprising the flow generator separate from the user interface and a housing further comprising a water source, an air delivery tube connecting the outlet of the flow generator with the interface passage, and a water tube provided for flow of water from the water source to a humidifier port in the interface passage.

19. The apparatus of claim 18, further comprising the water tube positioned within a lumen of the air delivery tube.

20. The apparatus of claim 18, further comprising the water tube configured to be external to the air delivery tube.

21. The apparatus of claim 1, further comprising the humidifier having a water source configured into the user interface.

22. The apparatus of claim 21, further comprising the flow generator integrated into the user interface.

23. Apparatus for providing positive airway pressure for the treatment of sleep apnea, chronic pulmonary obstruction and snoring, the apparatus comprising:
- a flow generator configured to provide air at a pressure of 4-20 cm of water at an outlet;
- a user interface comprising support bands configured to retain the user interface on the head of a user, an interface passage in fluid communication with the flow generator outlet and having a lumen, and a mask having a chamber and connected to the interface passage so that pressurized air may be delivered from the lumen into the chamber of the mask, the mask being configured to be positioned in communication with an airway of the user to provide a generally sealed connection to the user for the delivery of the pressurized air for inhalation, the interface passage having at least one vent therein;
- at least one vent valve associated with the at least one vent; and
- a humidifier configured to introduce water into the interface passage at a position distal to both the flow generator and the at least one vent, the at least one vent valve substantially in a substantially closed position in the presence of a low pressure condition and in a open position during the presence of a high pressure condition.

24. The apparatus of claim 23, wherein the low pressure condition is produced by inhalation by the user, and the high pressure condition is produced by exhalation of the user.

* * * * *